US006911826B2

(12) United States Patent
Plotnikov et al.

(10) Patent No.: US 6,911,826 B2
(45) Date of Patent: Jun. 28, 2005

(54) PULSED EDDY CURRENT SENSOR PROBES AND INSPECTION METHODS

(75) Inventors: Yuri Alexeyevich Plotnikov, Niskayuna, NY (US); Thomas James Batzinger, Burnt Hills, NY (US); Shridhar Champaknath Nath, Niskayuna, NY (US); Sandeep Kumar Dewangan, Krnataka (IN); Carl Stephen Lester, Porter Corners, NY (US); Kenneth Gordon Herd, Schenectady, NY (US); Curtis Wayne Rose, Mechanicville, NY (US)

(73) Assignee: General Electric Company, Niskayuna, NY (US)

( * ) Notice: Subject to any disclaimer, the term of this patent is extended or adjusted under 35 U.S.C. 154(b) by 0 days.

(21) Appl. No.: 10/727,401

(22) Filed: Dec. 3, 2003

(65) Prior Publication Data

US 2004/0245997 A1 Dec. 9, 2004

Related U.S. Application Data

(63) Continuation-in-part of application No. 09/681,824, filed on Jun. 12, 2001, now Pat. No. 6,720,775.

(51) Int. Cl.$^7$ .................. G01N 27/82; G01R 33/12; G01R 33/00; G01R 31/28
(52) U.S. Cl. ............... 324/529; 324/240; 324/242; 324/238; 324/262
(58) Field of Search .................. 324/240, 242, 324/232, 262, 238, 529

(56) References Cited

U.S. PATENT DOCUMENTS

| | | | |
|---|---|---|---|
| 3,875,502 A | 4/1975 | Neumaier | 324/241 |
| 4,188,577 A | 2/1980 | Mhatre et al. | 324/220 |
| 4,292,589 A | 9/1981 | Bonner | 324/221 |
| 4,495,466 A | 1/1985 | Lakin | 324/242 |
| 4,843,319 A | 6/1989 | Lara | 324/240 |
| 4,990,851 A | 2/1991 | Spies | 324/240 |
| 5,056,049 A | 10/1991 | O'Neill | 702/55 |
| 5,391,988 A | 2/1995 | Kitagawa | 324/225 |
| 5,434,506 A | 7/1995 | Flora | 324/242 |
| 5,491,409 A * | 2/1996 | Flora et al. | 324/242 |
| 5,659,248 A | 8/1997 | Hedengren et al. | 324/242 |

(Continued)

FOREIGN PATENT DOCUMENTS

| | | |
|---|---|---|
| EP | 0512796 | 5/1992 |
| EP | 05330440 | 9/1992 |

OTHER PUBLICATIONS

R. Rempt, Scanning with Magnetoresistive Sensors for Subsurface Corrosion, Review of Progress in Quantitative Nondestructive Evaluation, vol. 21, 2002 American Institute of Physics, pp. 1771–1778.

Y. A. Plotnikov et al., Defect Characterization in Multi–Layered Conductive Components with Pulsed Eddy Current, vol. 21, 2002 American Institute of Physics, pp. 1976–1983.

*Primary Examiner*—Anjan Deb
*Assistant Examiner*—John Teresinski
(74) *Attorney, Agent, or Firm*—Penny A. Clarke; Patrick K. Patnode

(57) ABSTRACT

A pulsed eddy current sensor probe includes a sensor array board. A number of sensors are arranged on the sensor array board and are operable to sense and generate output signals from the transient electromagnetic flux in a part being inspected. Each of the sensors has a differential output with a positive and a negative output. At least one drive coil is disposed adjacent to the sensors and is operable to transmit transient electromagnetic flux into the part. A first and a second multiplexer are arranged on the sensor array board and are operable to switch between the sensors. The first and second multiplexers are connected to the positive and negative outputs of the sensors, respectively.

27 Claims, 9 Drawing Sheets

U.S. PATENT DOCUMENTS

| | | | |
|---|---|---|---|
| 6,037,768 A | 3/2000 | Moulder et al. | 324/225 |
| 6,124,712 A | 9/2000 | Chaiken | 324/326 |
| 6,150,809 A * | 11/2000 | Tiernan et al. | 324/238 |
| 6,259,826 B1 | 7/2001 | Pollard et al. | 382/284 |
| 6,344,741 B1 | 2/2002 | Giguere et al. | 324/240 |
| 6,366,085 B1 | 4/2002 | Yeshurun et al. | 324/263 |
| 6,504,363 B1 | 1/2003 | Dogaru et al. | 324/235 |
| 6,573,721 B1 | 6/2003 | Cull | 324/336 |
| 6,720,775 B2 * | 4/2004 | Plotnikov et al. | 324/529 |

* cited by examiner

PULSED EDDY CURRENT SENSOR PROBES AND INSPECTION METHODS

CROSS REFERENCE TO RELATED APPLICATIONS

This is a continuation in part of application Ser. No. 09/681,824, filed Jun. 12, 2001, now U.S. Pat. No. 6,720,775 which is hereby incorporated by reference in its entirety.

BACKGROUND OF THE INVENTION

The present invention generally relates to nondestructive evaluation of metallic structures and, more particularly, is concerned with pulsed eddy current linear and two-dimensional sensor array probes for electrically conducting component inspection.

As the commercial and military aircraft fleets age, the development of reliable and accurate techniques for inspecting aircraft components become increasingly important. Nondestructive evaluation (NDE) of aircraft components is used to inspect aircraft components, while maintaining aircraft and component integrity. Corrosion and fatigue are potential sources of damage to the airframe, which may cause subsurface flaws. The presence of both surface cracks and subsurface flaws in metallic structures, such as aircraft skin structures, have the potential to lead to component failure. Various inspection methods have been used for crack and flaw detection with varying degrees of success.

One prior art inspection method uses eddy current probes, which can give an indication of depth to ascertain crack and flaw severity in conducting components. More particularly, eddy current inspection with harmonic excitation is a commonly used technique for nondestructive testing of aircraft skin. Eddy current inspection is based on the principle of electromagnetic induction. Typically, a drive coil is employed to induce eddy currents into the material under inspection. A magnetic field sensor such as inductive coil, Giant Magnetoresistive (GMR) sensor or Hall effect element detects secondary magnetic fields resulting from the eddy currents. The depth of the induced eddy currents depends on the frequency of the excitation current. Low frequency eddy currents can penetrate several conductive layers of a layered structure, which is advantageous for inspecting aircraft structures, such as lap joints, relative to other inspection techniques, such as ultrasonic and thermal inspection methods, which require mechanical or thermal coupling between the layers, respectively.

A variety of approaches have been proposed to increase the sensitivity and convenience of eddy current inspection. For example, the pulsed eddy current inspection technique was developed to overcome problems of conventional eddy current inspection associated with harmonic (sinusoidal) excitation. An example of this approach is given in the article "Measurement of Coating Thicknesses by Use of Pulsed Eddy Current" written by Donald L. Waidelich and published in the Nondestructive Testing Journal in 1956, pages 14–15. More recently, U.S. Pat. No. 6,037,768, entitled "Pulsed Eddy Current Inspections and the Calibration and Display of Inspection Results," describes a method for forming eddy current images from data acquired by a single probe using pulsed excitation. However, U.S. Pat. No. 6,037,768 is directed to inspecting a sample for flaws by mechanically scanning a single probe in two dimensions. Naturally, achieving full coverage with a single eddy current probe is very time consuming.

U.S. Pat. No. 6,124,712, entitled "Apparatus and Method for Imaging Metallic Objects Using an Array of Giant Magnetoresistive Sensors," describes application of a two-dimensional array of GMR sensors for graphical representation of detected metallic objects. U.S. Pat. No. 6,150,809, entitled "Giant Magnetoresistive Sensors and Sensor Arrays for Detection and Imaging of Anomalies in Conductive Materials," describes the use of GMR sensors for nondestructive evaluation of conductive materials. However, these patents are not directed to the use of pulsed eddy currents, nor to data collection and processing techniques that can be used to form a two-dimensional image of a detected flaw.

Consequently, a need still exists for an innovation that will improve the productivity of eddy current inspection of airframes to permit detailed, periodic inspection of aircraft. Moreover, there exists a need for an improved eddy current inspection technique to achieve full coverage of the inspection area, to inspect for subsurface defects and defects in layered components, and to efficiently form two-dimensional images of detected flaws.

BRIEF DESCRIPTION

Briefly, in accordance with one embodiment of the present invention, a pulsed eddy current (PEC) sensor probe is described. The PEC sensor probe includes a sensor array board and a number of sensors arranged on the sensor array board. The sensors are operable to sense and generate output signals from the transient electromagnetic flux in a part being inspected. Each of the sensors has a differential output with a positive and a negative output. The PEC sensor probe also includes at least one drive coil disposed adjacent to the sensors and operable to transmit transient electromagnetic flux into the part being inspected. A first multiplexer is arranged on the sensor array board and is operable to switch between the sensors. A second multiplexer is also arranged on the sensor array board and is operable to switch between the sensors. The first multiplexer is connected to the positive outputs of the sensors, and the second multiplexer is connected to the negative outputs of the sensors.

Another PEC sensor probe embodiment is also described. The PEC sensor probe includes a number of sensor array boards. A number of sensors are arranged in a linear array on each of the sensor array boards and are operable to sense and generate output signals from the transient electromagnetic flux in the part being inspected. Each of the sensors has a differential output with a positive and a negative output. The PEC sensor probe also includes a number of drive coils disposed adjacent to the sensors, which are operable to transmit transient electromagnetic flux into the part being inspected, and a number of first and second multiplexers. Each of the first and second multiplexers is arranged on a respective one of the sensor array boards and is operable to switch between the sensors on the respective sensor array board. Each of the first multiplexers is connected to the positive outputs of the sensors on the respective sensor array board, and each of the second multiplexers is connected to the negative outputs of the sensors on the respective sensor array board. The sensor array boards are arranged to form a two-dimensional sensor array.

A method embodiment is also described. The method of inspecting a part includes positioning a linear array of sensors adjacent to a surface of the part. Each of the sensors has an axis of sensitivity aligned substantially normal to the surface of the part. The method further includes generating a magnetic flux that is oriented in a direction substantially along the axis of sensitivity of the sensors to transmit transient electromagnetic flux into the part, and sensing the transient electromagnetic flux in the part being inspected and generating a differential output signal using one of the sensors. The generation of the magnetic field and the sensing and generating the differential output signal using one of the sensors are repeated for at least a subset of the sensors in the linear array, to acquire a number of the differential output signals. Each of the differential output signals includes a positive and a negative output.

Another method embodiment is also described. The method of inspecting a part includes positioning a two dimensional sensor array adjacent to a surface of the part. The two dimensional sensor array includes a number of linear arrays of sensors. Each of the linear arrays is disposed on a respective sensor array board, and each of the sensors has an axis of sensitivity aligned substantially normal to the surface of the part. The method further includes generating a magnetic flux that is oriented in a direction substantially along the axis of sensitivity of the sensors to transmit transient electromagnetic flux into the part, and sensing the transient electromagnetic flux in the part being inspected and generating a differential output signal using one of the sensors. The generation of the magnetic field and the sensing and generating the differential output signal using one of the sensors are repeated for at least a subset of the sensors in respective ones of at least a subset of the linear arrays, to acquire a number of the differential output signals. Each of the differential output signals includes a positive and a negative output.

BRIEF DESCRIPTION OF THE DRAWINGS

These and other features, aspects, and advantages of the present invention will become better understood when the following detailed description is read with reference to the accompanying drawings in which like characters represent like parts throughout the drawings, wherein.

DETAILED DESCRIPTION

Figure 1:
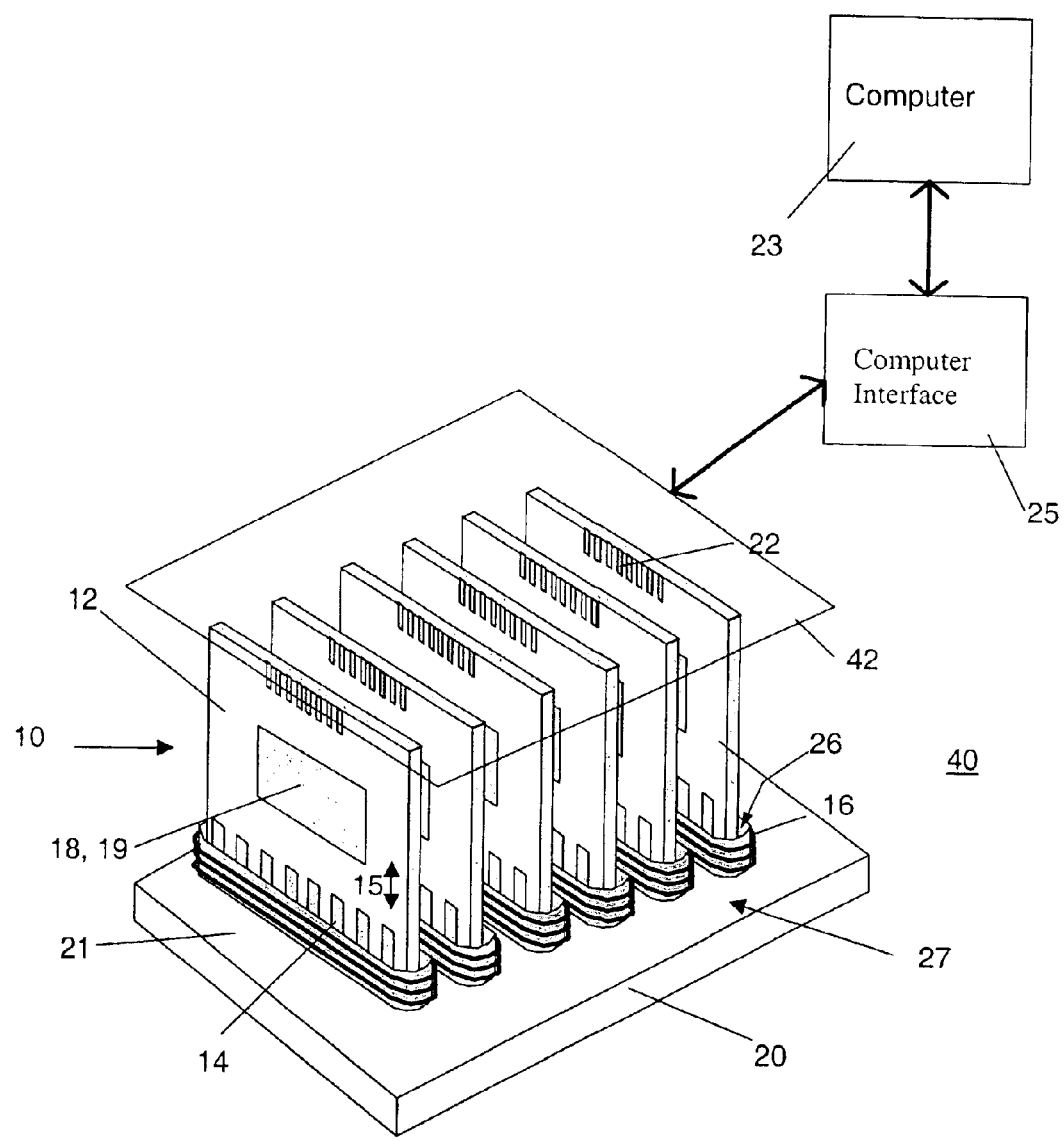
FIG. 1 is a perspective view of a two-dimensional arrangement of linear array pulsed eddy current sensor probes.

A pulsed eddy current (PEC) sensor probe 10 embodiment of the invention is described with reference to FIGS. 1–4. As shown, for example in FIGS. 1 and 2, the PEC sensor probe 10 includes a sensor array board 12. An exemplary sensor array board 12 is a printed circuit board (PCB) 12. The PEC sensor probe 10 further includes a number of sensors 14 arranged on the sensor array board 10. The sensors 14 are operable to sense and generate output signals from the transient electromagnetic flux in a part 20 being inspected, and each of the sensors 14 has a differential output comprising a positive and a negative output. An exemplary part 20, for example a conducting component, is indicated in FIG. 1. The PEC sensor probe 10 further includes at least one drive coil 16 disposed adjacent to the sensors, as indicated for example, in FIGS. 1 and 3. The drive coil 16 is operable to transmit transient electromagnetic flux into the part 20 being inspected. For the exemplary embodiment of FIG. 3, the drive coil 16 is a multiple-turn solenoid of generally rectangular configuration surrounding the sensors 14.

Figure 4:
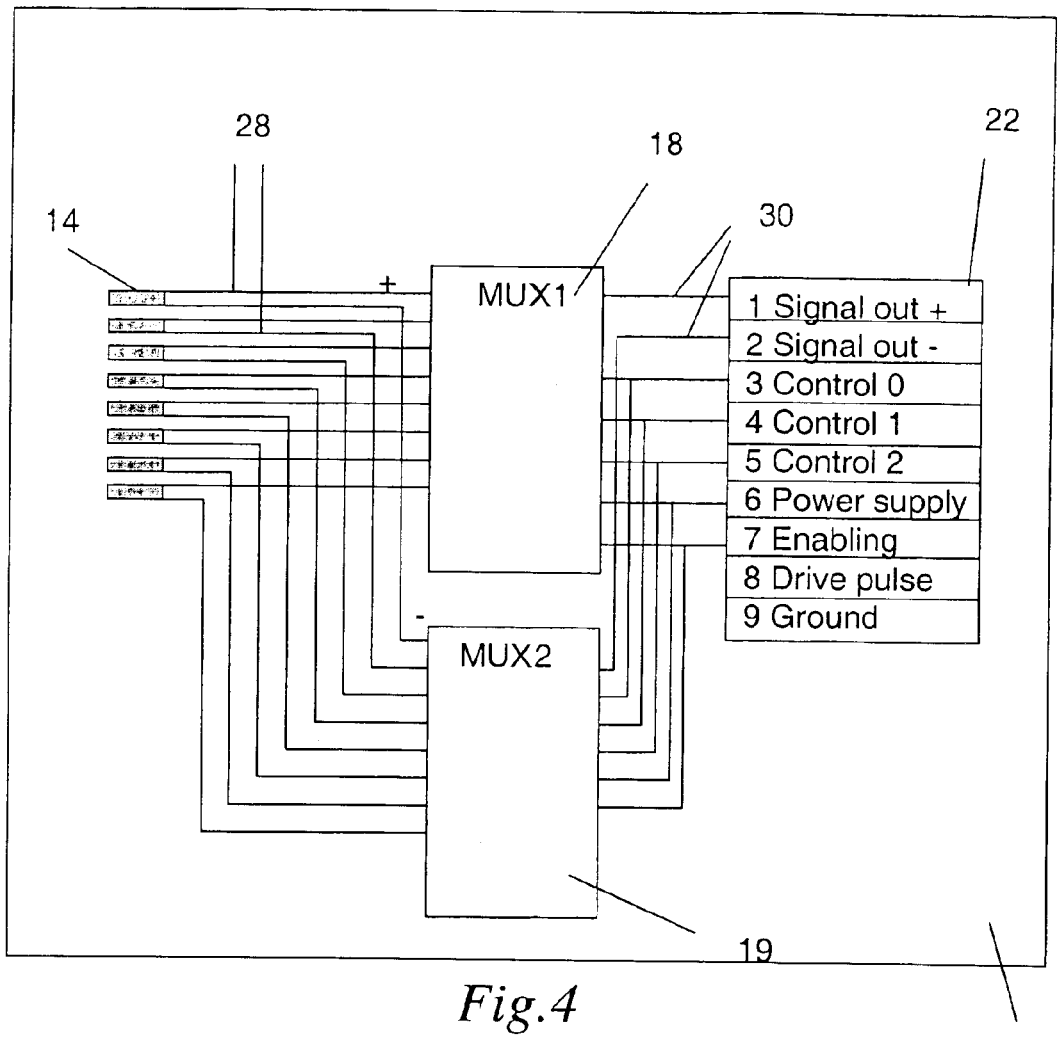
FIG. 4 illustrates an exemplary on-board multiplexing of the sensor output signals on an exemplary linear array pulsed eddy current sensor probe.

The PEC sensor probe 10 further includes a first and a second multiplexer 18, 19 arranged on the sensor array board 12. An exemplary multiplexer 18, 19 is an analog multiplexer 18, 19. The multiplexers 18, 19 are operable to switch between the sensors 14, as indicated for example in FIG. 4. For example, the multiplexers 18, 19 switch the sensors 14 using signal lines 28 that extend between each of the sensors 14 and the multiplexers 18, 19. As shown in FIG. 4, the first multiplexer 18 is connected to the positive outputs of the sensors 14, and the second multiplexer 19 is connected to the negative outputs of the sensors 14. In this manner, the sensors 14 are separately activated for sensing and generating output signals from the transient electromagnetic flux in the part 20 being inspected. The process of multiplexing the sensor output employing multiplexers located on the array boards 12 is termed "on-board multiplexing" herein. Beneficially, on-board multiplexing of the transient signals from the sensors 14 renders the PEC sensor probe 10 highly resistive to noise, reduces the number of signal lines connecting the sensors 14 to the computer interface 25 and facilitates rapid data acquisition, suitable for real-time imaging.

Figure 5:
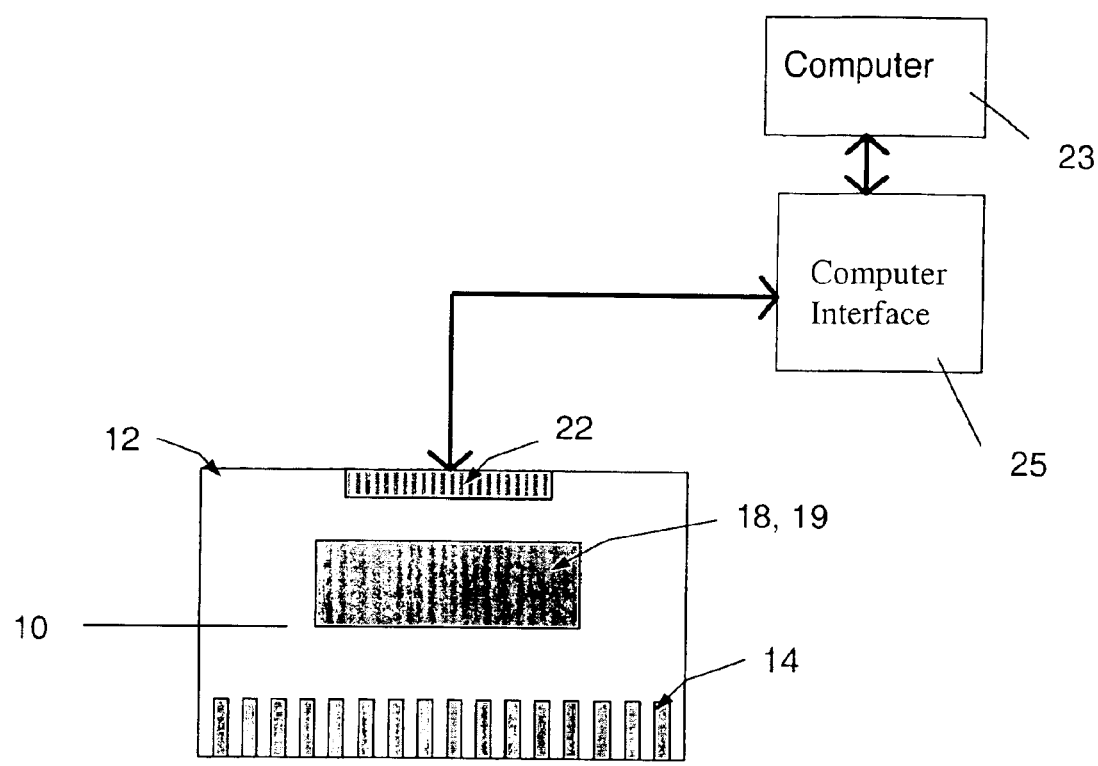
FIG. 5 shows the linear array pulsed eddy current sensor probe of FIG. 2 connected to a computer via a computer interface.

In order to connect the PEC sensor probe 10 to other devices, the PEC sensor probe 10 further includes a connector 22 operable to connect the multiplexers 18, 19 to an external device 23, as shown for example in FIG. 5. For example, the connector 22 connects to the multiplexers 18, 19 through connections 30 on the sensor array board 12, as indicated in FIG. 4, for example. An exemplary external device 23 is a computer 23, and the connector may connect to the computer through other circuitry, such as an amplifier (not shown), analog to digital converter (not shown), and a computer interface 25. For the exemplary embodiments of FIGS. 1, 2, and 5, the connector 22 is disposed on the sensor array board 12.

According to one embodiment, customized software stored in the computer 23 controls the data acquisition, processes the acquired data and displays the results, for example on a monitor (not shown). For example, the computer sends the exemplary control signals shown in FIG. 4 to the connector 22 of the PEC sensor probe 10 via the computer interface 25. In this manner the electronic switching of the sensors outputs is achieved by means of the computer interface 25 after completion of the data collection cycle for each sensor 14.

Figure 2:
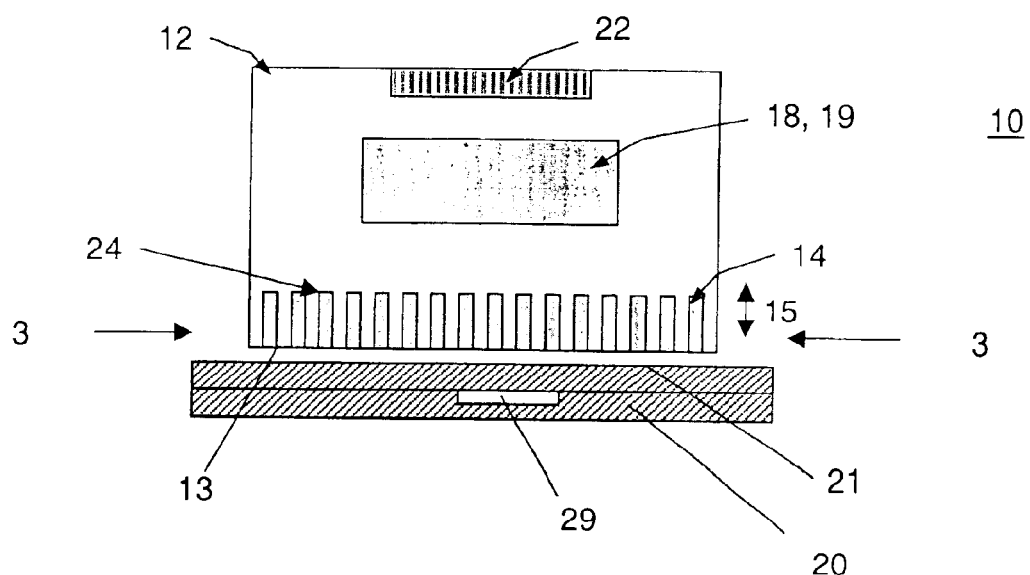
FIG. 2 is a front view of one of the linear array pulsed eddy current sensor probes of FIG. 1 with the drive coil omitted.
Figure 3:
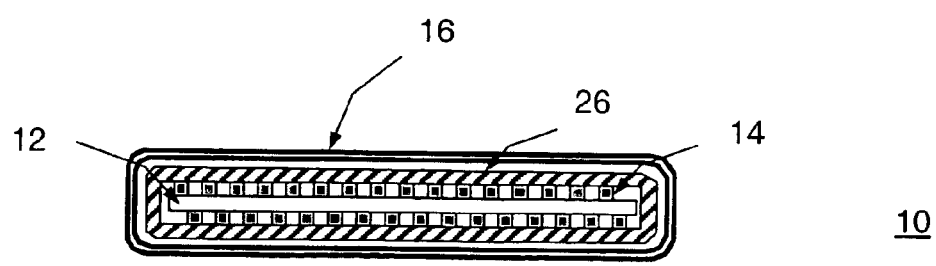
FIG. 3 is a cross-section view taken along the line 3—3 of the linear array pulsed eddy current sensor probe of FIG. 2 with added drive coil and magnetic shielding.

For the embodiment of FIGS. 1, 2 and 3, the sensors 14 form a linear array 24 on the sensor array board 12, as indicated in FIG. 2. According to a more particular embodiment, the PEC sensor probe 10 further includes a magnetic shielding 26 disposed between the sensors 14 and the drive coil 16, as indicated in FIGS. 1 and 3, for example. Beneficially, the magnetic shielding 26 reduces the direct cross-talk between the drive coil 16 and the sensors 14 and concentrates magnetic flux for deeper flaw sensing.

For the embodiment of FIGS. 1 and 2, the sensors 14 are positioned at an edge 13 of sensor array board, and each of sensors has an axis of sensitivity 15 that is oriented substantially normal to edge, as indicated in FIG. 2. Exemplary sensors 14 include magnetic field sensors such as wound or deposited coil sensors, Hall elements, flux gate sensors, and Giant Magnetoresistive (GMR) sensors. According to a particular embodiment, the sensors 14 are GMR sensors 14. The output of a GMR sensor 14 is proportional to the normal (relative to the surface of the part 21) component of the transient electromagnetic flux under the GMR sensor 14. Change of the sensor output relative to the flux over a reference area indicates the presence of a flaw in the part 20. For the exemplary embodiment of FIGS. 1 and 3, the drive coil 16 extends around the linear array 24 of GMR sensors 14 and is operable to generate a magnetic flux that is oriented in a direction substantially along the axis of sensitivity 15 of the GMR sensors. Beneficially, by aligning the axis of sensitivity 15 for the GMR sensors 14 in parallel to the principal axis of the drive coil 16, a higher sensitivity to subsurface defects is achieved.

Another pulsed eddy current (PEC) sensor probe 40 embodiment is described with reference to FIGS. 1, 4, 6 and 7. As shown for example, in FIG. 1, the PEC sensor probe 40 includes a number of sensor array boards 12. A number of sensors 14 are arranged in a linear array 24 on each of the sensor array boards 12. The linear array 24 arrangement is described above with reference to FIG. 2, for example. As discussed above, the sensors 14 are operable to sense and generate output signals from the transient electromagnetic flux in a part 20 being inspected, and each of sensors 14 has a differential output comprising a positive and a negative output. An exemplary part 20 is indicated in FIG. 8. A number of drive coils 16 are disposed adjacent to the sensors 14 and are operable to transmit transient electromagnetic flux into the part 20 being inspected. The PEC sensor probe 40 also includes a number of first and second multiplexers 18, 19. As indicated, for example in FIG. 4, each of the first and second multiplexers 18, 19 is arranged on a respective one of the sensor array boards 12. As discussed above with respect to FIG. 4, each of the first and second multiplexers 18, 19 is operable to switch between the sensors 14 on the respective sensor array board 12. As indicated in FIG. 4, each of the first multiplexers 18 is connected to the positive outputs of the sensors 14 on the respective sensor array board 12, and each of the second multiplexers 19 is connected to the negative outputs of the sensors 14 on the respective sensor array board 12. As shown, for example, in FIG. 1, the sensor array boards 12 are arranged to form a two dimensional sensor array 27. That is, the sensor boards 12 are arranged such that the respective linear arrays 24 of sensors 14 on the sensors boards 12 form the two-dimensional sensor array 27. Beneficially, providing electronic switching via multiplexers 18, 19 for the sensors 14 facilitates high speed imaging and eliminates the need for time-consuming mechanical scanning with a single sensor or smaller sensor array, while covering an area equal to the size of the array 27. In addition, this arrangement permits the use of a large number of sensors, for example, several hundred sensors 14, which are closely spaced, for example separated by about 0.5 mm, thereby facilitating large-area, precise imaging of flaws in the inspected component 20.

For the exemplary embodiment of FIG. 1, at least one drive coil 16 is connected to a respective one of each of the sensor array boards 12. More particularly, one drive coil 16 is provided for each of the sensors array boards 12 in the PEC sensor probe 40 shown in FIG. 1. One of the linear arrays 24 of sensors 14 of the PEC sensor probe 40 is shown in front view in FIG. 2, with the drive coil 16 and any magnetic shielding 26 omitted. For the exemplary embodiment of FIG. 2, the sensors 14 are positioned at an edge 13 of the respective sensor array board 12 to form the respective linear array 24. More particularly, each of the sensors 14 has an axis of sensitivity 15 that is oriented substantially normal to the edge 13 of the respective sensor array board 12. For the exemplary embodiment of FIG. 1, each of the drive coils 16 extends around the respective linear array 24 of sensors 14 and is operable to generate a magnetic field that is oriented in a direction substantially along the axis of sensitivity 15 of the sensors 14. Exemplary sensors 14 are discussed above, and according to a particular embodiment, each of the sensors 14 is a GMR sensor with an axis of sensitivity 15 that is oriented substantially normal to the edge 13 of the respective sensor array board 12. To reduce cross-talk between the sensors 14 and the respective drive coils 16, the sensor probe 40 includes a number of magnetic shieldings 26, according to a more particular embodiment. Each of the magnetic shieldings 26 is disposed between the sensors 14 and the respective drive coil 16, as indicated for example in FIGS. 1 and 3.

For the exemplary embodiment of FIG. 1, the PEC sensor probe 40 further includes a number of connectors 22. As shown, at least one of the connectors 22 is disposed on each of the sensor array boards 12. Each of the connectors 22 is operable to connect to the first and second multiplexers 18, 19 on the respective one of the sensor array boards 12, as indicated in FIG. 4, for example. According to a more particular embodiment, the PEC sensor probe 40 includes a motherboard 42 connected to each of connectors 22. An exemplary motherboard 42 is indicated in FIG. 1. As shown, the motherboard 42 may be used to connect the PEC sensor probe 40 to an external device, such as a computer 23 or other data acquisition or measurement system 23, via a computer interface 25, which may include circuitry such as amplifiers (not shown) and analog-to-digital converters (not shown). Specialized software may be run on the computer 23 to control the data acquisition, process the acquired data and display the results, for example on a monitor. An exemplary image for display and/or analysis is in the form of a two-dimensional image, where each pixel corresponds to the processed data associated with a respective one of the sensors 14. Using the computer 23, a wide variety of digital image processing methods can be employed to obtain better representation of a flaw.

Figure 6:
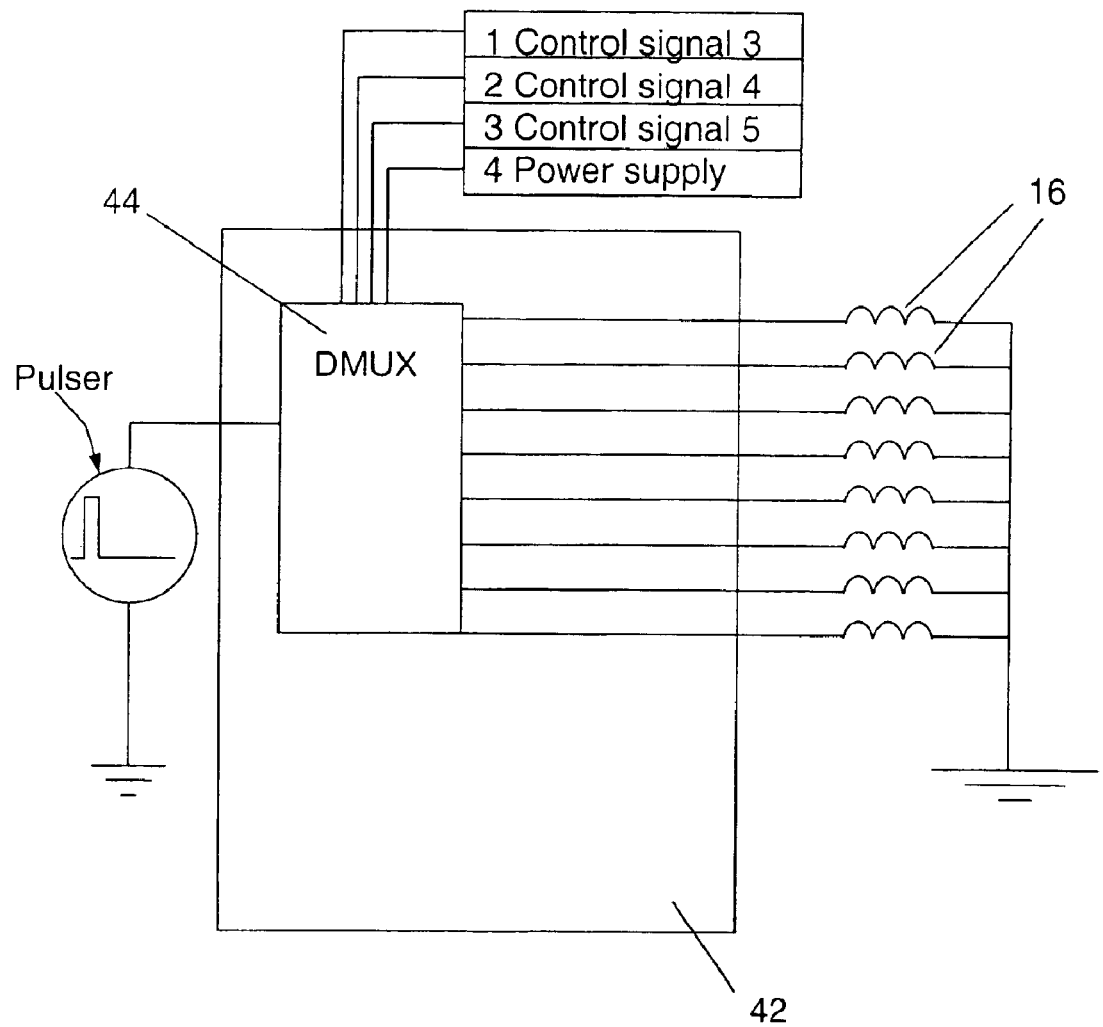
FIG. 6 illustrates an exemplary means for selectively driving a number of drive coils disposed on respective sensor array boards for a two dimensional sensor array.

Activation of the drive coils 16 is described with reference to FIG. 6. As shown in FIG. 6, the PEC sensor probe 40 includes a demultiplexer 44 disposed on the motherboard 42. For this exemplary embodiment, at least one drive coil 16 is connected to a respective one of each of the sensor array boards 12. For example, one drive coil 16 is provided for each of the sensor array boards 12, as shown in FIG. 1. As indicated in FIG. 1, the demultiplexer 44 is operable to receive a number of control signals and a number of drive pulses and to selectively drive each of the drive coils 16 in response to the control signals. The drive pulses are supplied by a pulse generator 50. An exemplary pulse generator 50 supplies current pulses to the drive coils 16 with a repetition rate of 100 Hz. The control signals may be generated by the computer 23 and supplied to the demultiplexer 44 via the computer interface 25, which are shown in FIG. 1.

Figure 7:
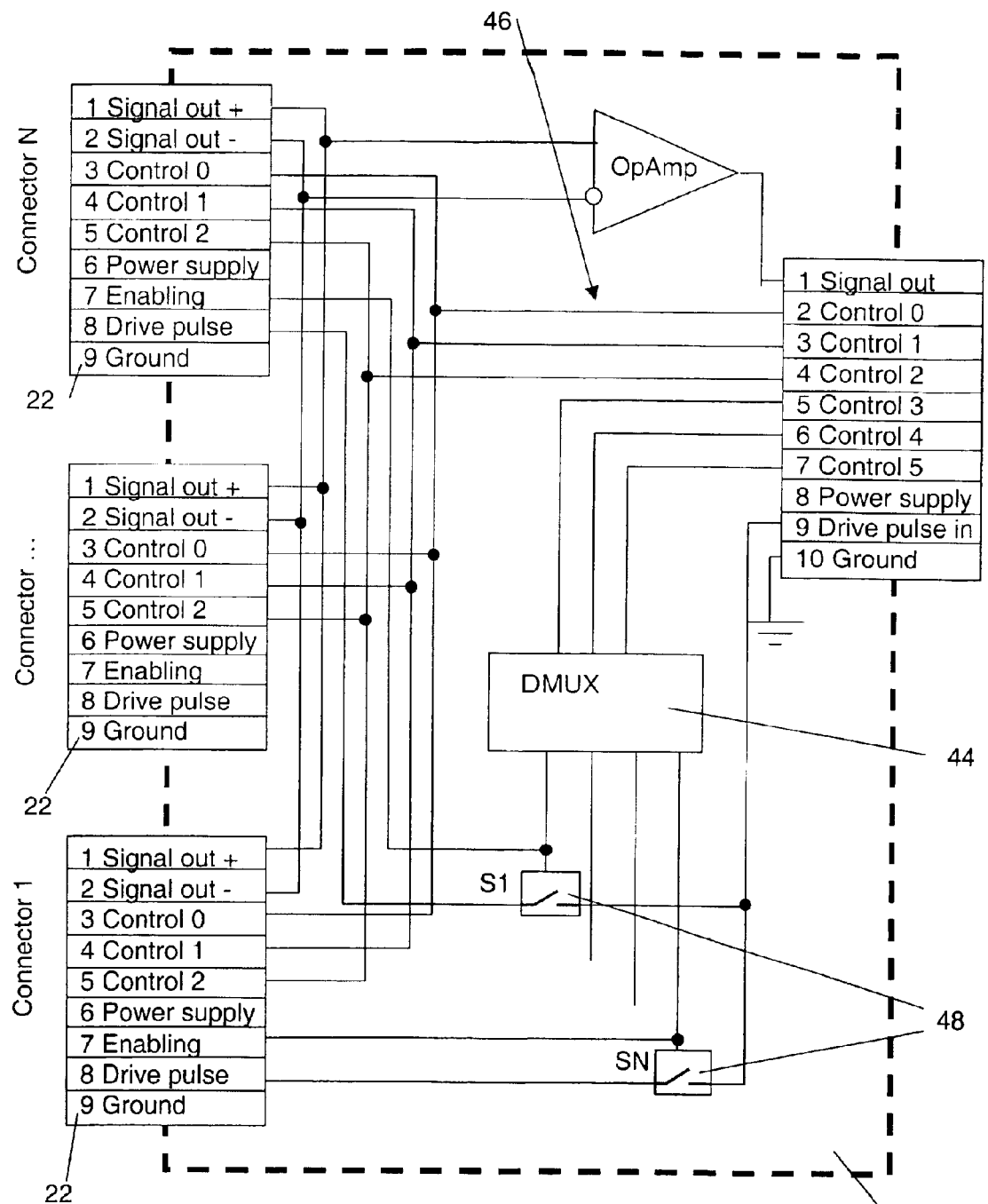
FIG. 7 illustrates an exemplary enabling circuit for selectively enabling each of the sensor array boards in the exemplary pulsed eddy current sensor probe of FIG. 1.
Figure 8:
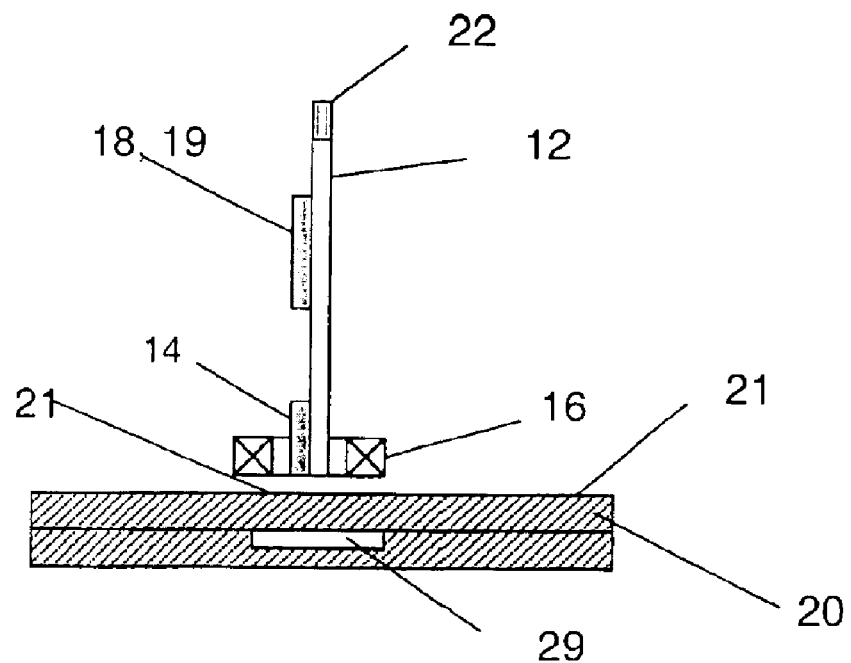
FIG. 8 is a side view of the linear array pulsed eddy current sensor probe of FIGS. 2 and 3 positioned above an exemplary part with a subsurface defect.

FIG. 7 illustrates an exemplary enabling circuit for selectively enabling each of the sensor array boards 12 in the PEC sensor probe 40 of FIG. 1. As noted above, for the embodiment of FIG. 1, at least one drive coil 16 is connected to a respective one of each of the sensor array boards 12. As shown in FIG. 7, the PEC sensor probe 40 includes an enabling circuit 46 adapted to selectively enable each of the sensor array boards 12 via the respective connector 22 for driving the respective drive coil 16 and for collecting a number of output signals using the sensors 14 in the linear array 24 on the respective sensor array board 12. As shown, the exemplary enabling circuit 46 includes a demultiplexer 44 and a number of switches 48 disposed on the motherboard 42. The demultiplexer 44 is operable to receive a number of control signals and a number of drive pulses and to selectively drive each of the drive coils 16 in response to the control signals via the respective connector 22, as discussed above with respect to FIG. 6. For example, the computer 23 sends the exemplary control signals shown in FIG. 7 to the motherboard 42 via the computer interface 25. In response, the enabling circuit 46 selectively enables each of the sensors array boards 12 in the PEC sensor probe 40 via the connectors 22 for the respective sensor array boards 12. Once enabled, the control signals are received by the first and second multiplexers 18, 19 on the enabled sensor array board 18, 19, for data collection via the computer interface 25 and electronic switching of the sensors outputs for each sensor 14 in the respective linear array 24. In this manner, the PEC sensor probe 40 provides two level communication, where the first level corresponds to on-board switching between the sensors 14 on a given sensor array board 12, and the second level corresponds to enabling each of the sensor array boards 12 in the PEC sensor probe 40 to pulse the respective drive coil 16 and collect data from the respective linear array 24. Beneficially, this two level communication facilitates the use of large two-dimensional arrays 27, for example having hundreds of sensors 14. The use of large two-dimensional arrays 27 facilitates area-by-area scans, which enhance inspection productivity relative to scans with single sensors or small numbers of sensors. Moreover, this two-level communication scheme also provides rapid communication of signal outputs from the sensors 14, thereby facilitating real-time imaging, for example updating a two-dimensional image several times per second. The resulting rapid image update rate helps an operator to better understand the shape of a detected flaw in the part 20 by changing the position of the probe 40 relative to the part.

The following are exemplary fabrication processes for the PEC sensor probes 10, 40. GMR sensors 14 may be formed on printed circuit boards 12 using complementary metal-oxide semiconductor (CMOS) deposition techniques or in die form. According to a particular embodiment, the GMR sensors 14 are closely spaced to one another, for example separated by as little as 0.5 mm. Beneficially, forming the GMR sensors 14 in die form, as compared with IC form, permits high-density deposition of the GMR sensors 14, which in turn facilitates the use of smaller PCBs 12 and thus smaller PEC sensor probes 10, 40. In addition, closer spacing between the GMR sensors 14 improves the resolution of the probe. More particularly, the GMR sensors 14 are positioned near the edge 13 of the printed circuit board (PCB) 12 with their axis of sensitivity 15 oriented perpendicular to the edge 13 of the PCB 12.

Figure 9:
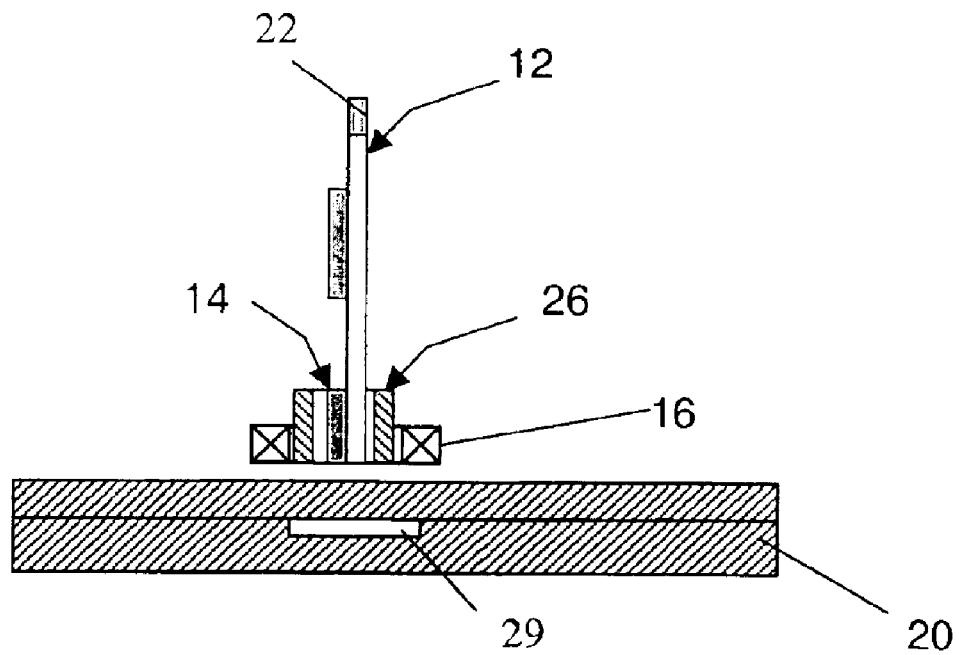
FIG. 9 illustrates the inspection method of FIG. 8, where the pulsed eddy current sensor probe includes magnetic shielding.

An inspection method embodiment of the invention is described with reference to FIGS. 2, 8 and 9. As indicated in FIG. 2, the method of inspecting a part 20 includes positioning a linear array 24 of sensors 14 adjacent to a surface 21 of the part, wherein each of the sensors 14 has an axis of sensitivity 15 aligned substantially normal to the surface 21 of the part 20, as indicated in FIG. 2. FIGS. 8 and 9 show the arrangement of FIG. 2 in side view. This can be accomplished, for example, by positioning the sensor array board 12 normally to the surface 21 of the part 20, as indicated in FIGS. 8 and 9. The inspection method further includes generating a magnetic field that is oriented in a direction substantially along the axis of sensitivity 15 of the sensors 14, to transmit transient electromagnetic flux into the part 20. The inspection method also includes sensing the transient electromagnetic flux in the part 20 being inspected and generating a differential output signal using one of the sensors 14. As noted above, each of the differential output signals has a positive and a negative output. The steps of generating the magnetic field and sensing and generating the differential output signal using one of the sensors 14 are repeated for at least a subset of the sensors 14 in the linear array 24 to acquire a number of the differential output signals. More particularly, these steps are repeated for each of the sensors 14 in the linear array 24. Still more particularly, the linear array 24 of sensors 14 is disposed on a sensor array board 12, as indicated in FIG. 2, for example, and the inspection method further includes performing on-board multiplexing to switch between the sensors 14. As discussed above, on-board multiplexing refers to the process of multiplexing the sensor outputs employing multiplexers 18, 19 located on the array board 12. Beneficially, by performing on-board multiplexing, provides rapid switching between the sensors 14, thereby enabling the use of a large number of sensors 14. In addition, real-time one-dimensional imaging of surface and subsurface defects 29 in conducting components 20 can be achieved using this method.

A transient electromagnetic signal obtained from a sensor 14 depends on its position relative to the drive coil 16 and on the geometry of the part 20 under the sensor 14. The probe 10, 40 is nulled on a reference region of the part 20, which is known to be flawless, and the transient responses of each of the sensors 14 is recorded, for example in a computer 23. During inspection, a response signal is compared to the signal obtained for the sensor 14 during the nulling phase, for example the response signal is subtracted from the signal obtained during the nulling phase. The resulting image of the flaw is based on the variations among the signal differences for the sensors 14 in the linear array 24.

According to a more particular embodiment, the inspection method further includes indexing and storing the differential output signals to indicate the respective sensors 14 used to generate the differential output signals. For example, the differential output signals are indexed by sensor 14 and stored in a data acquisition unit 23, such as a computer 23. Beneficially, by indexing the differential output signals for storage, the data is correlated with the respective sensors 14 used to collect the data. This in turn correlates the data with the spatial coordinates.

Figure 10:
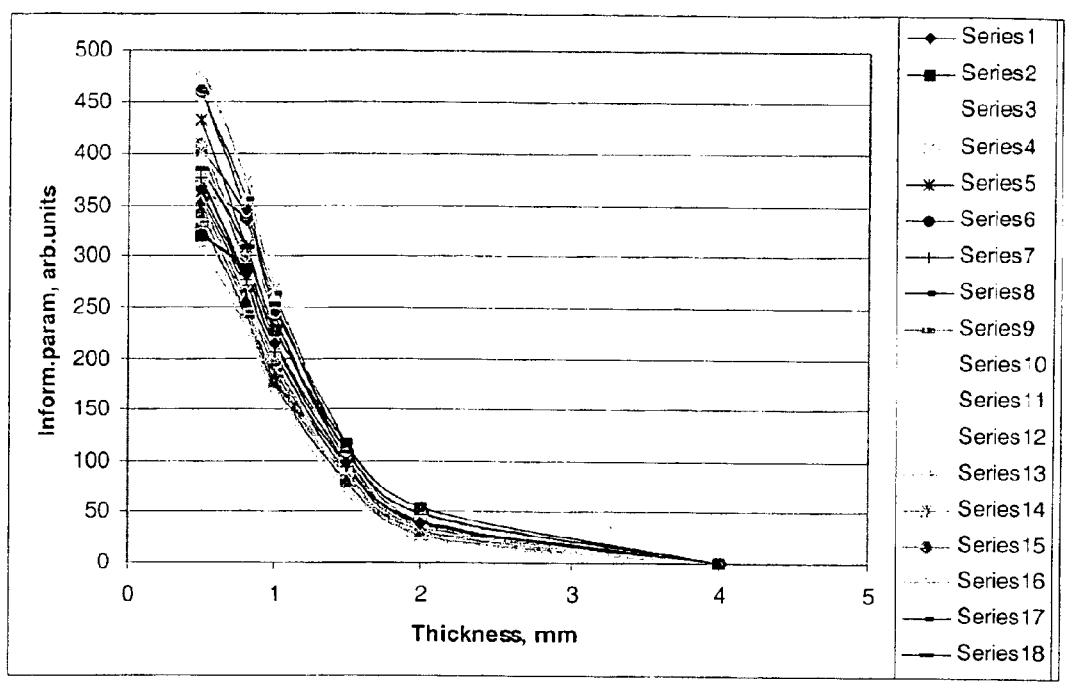
FIG. 10 shows exemplary calibration curves for a number of Giant Magnetoresistive sensors characterized by a sine informative parameter S.

According to a more particular embodiment, a calibration curve is generated for each of the sensors 14. Exemplary calibration curves are shown in FIG. 10 as a function of thickness. A number of informative parameter values are calculated for the differential output signals, each of the informative parameter values being associated with a respective one of the sensors 14. The informative parameter values are compared with the respective calibration curves to calibrate the sensors 14.

Beneficially, use of an informative parameter S provides a stable output because it is computed over a large time value, that is, it is computed for a number of data points. As discussed in commonly assigned, copending U.S. patent application Ser. No. 09/681,824, filed Jun. 12, 2001, a wide variety of algorithms can be used to compute the informative parameter for the sensors 14. One exemplary informative parameter S that can be used to form an image is the mean of the signal difference U during a fixed time interval $t_1-t_2$:

$$S(i, j) = \frac{1}{N}\sum_{n=1}^{N} U(i, j, n), \quad (1)$$

where i and j are the coordinates of the sensors 18 in the two-dimensional array and N is the number of sampled values of the signal difference U(i,j,n) during the time interval $t_1-t_2$.

Another exemplary informative parameter S can be computed by using a sine filter by convolving the signal difference U(i,j,n) with the sin( ) function:

$$S(i, j) = \frac{1}{N}\sum_{n=1}^{N} U(i, j, n)\sin\left(\frac{2\pi \cdot (n-1)}{N}\right). \quad (2)$$

Because the informative parameter S defined by the equation (2) is not sensitive to the constant level bias of the signal U, this algorithm was found to be effective in presence of an external magnetic field with constant level during the measurement cycle. In other words by computing the informative parameter using the sine filter, the different DC offsets associated with each of the respective sensors 14 is removed. These DC offsets are caused by static magnetic fields and the bias voltage of the signal circuits. Application of the discrete sine transform further provides low pass filtration of the transient signal. More generally, other discrete transforms (Fourier, Laplace, wavelet, etc.) applied in the time domain can also be used to compute the informative parameter S.

Beneficially, application of the sine transform to the signal from each of the sensors 14 plus the application of individual calibration functions provides high-quality imaging as well as quantitative assessment of part thickness. For example, to obtain a quantitative assessment of the wall thickness of a part, data is acquired, each spatial coordinate is indexed to identify the sensor 14 number corresponding to this point, the informative parameter is computed for each spatial coordinate (i.e., for each sensor 14), and the calibration curve for the respective sensor is applied yielding the wall thickness estimate for the respective spatial coordinate. By repeating these steps for each of the spatial coordinates (i.e., for each of the sensors 14), the wall thickness is determined for all spatial coordinates within the scan.

Figure 11:
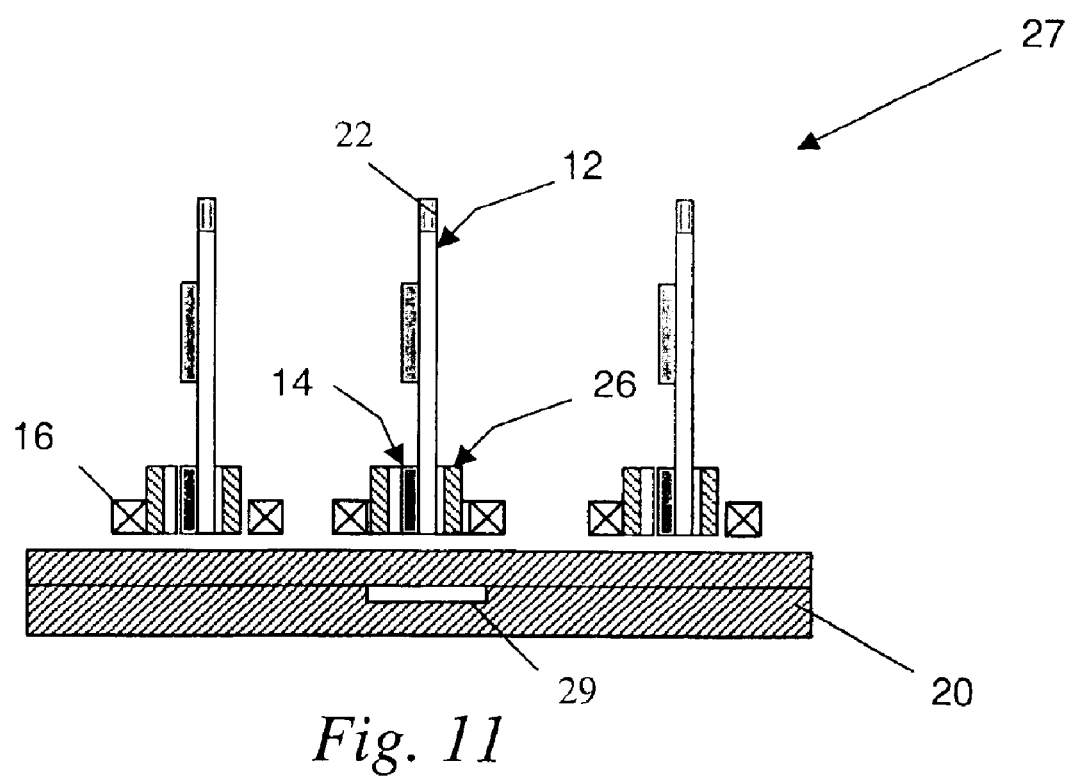
FIG. 11 illustrates an exemplary inspection method embodiment employing a two dimensional array of sensors.

Another inspection method embodiment of the invention is described with reference to FIGS. 1 and 11. FIG. 11 shows the arrangement of FIG. 1 in side view. As indicated in FIGS. 1 and 11, the method of inspecting a part 20 includes positioning a two dimensional sensor array 27 adjacent to a surface 21 of the part 20. As discussed above with respect to FIG. 1, the two-dimensional sensor array 27 is formed from a number of linear arrays 24 of sensors 14, and each of the linear arrays 24 is disposed on a respective sensor array board 12, as indicated in FIG. 1. Each of the sensors 14 has an axis of sensitivity 15 aligned substantially normal to the surface 21 of the part 20, as indicated in FIG. 1. A magnetic flux is generated that is oriented in a direction substantially along the axis of sensitivity 15 of the sensors 14 to transmit transient electromagnetic flux into the part 20, for example by energizing a respective one of the drive coils 16. The inspection method further includes sensing the transient electromagnetic flux in the part 20 being inspected and generating a differential output signal using one of the sensors 14. As noted above, each of the differential output signals has a positive and a negative output. The steps of generating the magnetic field and sensing and generating the differential output signal using one of the sensors 14 are repeated for at least a subset of the sensors 14 in each of at least a subset of the linear arrays 24 to acquire a number of the differential output signals. More particularly, these steps are repeated for each of the sensors 14 in a first one of the linear arrays 24, then for a second one of the linear arrays 24, and so on until data has been collected with each of the linear arrays 24 in the two dimensional sensor array 27.

The inspection method may further include indexing and storing the differential output signals to indicate the respective sensors 14 used to generate the differential output signals, as discussed above. In addition, the inspection method may further generating a calibration curve for each of the sensors 14 in the two dimensional array 27, calculating a number of informative parameter values for the differential output signals, where each of the informative parameter values is associated with a respective one of the sensors 14 in the two dimensional sensor array 27, and comparing the informative parameter values with the respective calibration curves to calibrate the sensors 14.

As explained in commonly assigned, copending U.S. patent application Ser. No. 09/681,824, a two-dimensional image may be formed by assigning a gray level to the amplitude of an informative parameter S that is computed for each individual sensor 14 in the two-dimensional array 27. Each element (pixel) of the image is located according to the spatial position of the sensor 14 in the array 27. Using a color map (also called a color palette), a color image is formed as the color values are given to each pixel of the gray scale image from the corresponding look-up tables.

For the exemplary embodiment of FIG. 1, each of the linear arrays 24 of sensors 14 is disposed on a respective one of the sensor array boards 12, and the inspection method further includes performing on-board multiplexing to switch between the sensors 14 within a respective one of the linear arrays 27. More particularly, for the exemplary embodiment of FIG. 1, a drive coil 16 is disposed on each of the sensor array boards 12. For this exemplary embodiment, the inspection method further includes enabling a respective one of the sensor array boards 12 and selectively driving the drive coil 16 on the respective sensor array board 12 to generate the magnetic field for transmitting transient electromagnetic flux into the part 20. The differential output signals are collected using the sensors 14 in the linear array 24 on the respective sensor array board 12. The steps of enabling, selectively driving and collecting are repeated for each of the sensor array boards 12 for collecting the differential output signals from the sensors 14 within each of the linear arrays 24 forming the two dimensional sensor array 27. These steps may be accomplished, for example, using the exemplary enabling circuit 46 discussed above with respect to FIG. 7. In this manner, two level communication is provided, where the first level corresponds to on-board switching between the sensors 14 on a given sensor array board 12, and the second level corresponds to enabling each of the sensor array boards 12 in the two dimensional array 27 to pulse the respective drive coil 16 and collect data from the respective linear array 24. Beneficially, this two level communication facilitates the use of large two dimensional arrays 27, thereby facilitating area-by-area scans, which enhance inspection productivity relative to scans with single sensors or small numbers of sensors. Moreover, this two-level communication scheme also provides rapid communication of signal outputs from the sensors 14, thereby facilitating real-time two-dimensional imaging of surface and subsurface defects 29 in conducting components 20, for example updating a two-dimensional image several times per second.

Although only certain features of the invention have been illustrated and described herein, many modifications and changes will occur to those skilled in the art. It is, therefore, to be understood that the appended claims are intended to cover all such modifications and changes as fall within the true spirit of the invention.

What is claimed is:

1. A pulsed eddy current sensor probe comprising: a sensor array board;
a plurality of sensors arranged on said sensor array board and operable to sense and generate output signals from the transient electromagnetic flux in a part being inspected, each of said sensors having a differential output comprising a positive and a negative output, wherein said sensors are positioned at an edge of said sensor array board, and each of said sensors has an axis of sensitivity that is oriented substantially normal to said edge;
at least one drive coil disposed adjacent to said sensors and operable to transmit transient electromagnetic flux into the part being inspected;
a first multiplexer arranged on said sensor array board and operable to switch between said sensors; and
a second multiplexer arranged on said sensor array board and operable to switch between said sensors,
wherein said first multiplexer is connected to the positive outputs of said sensors, and
wherein said second multiplexer is connected to the negative outputs of said sensors.

2. The pulsed eddy current sensor probe of claim 1, further comprising a connector operable to connect said multiplexers to an external device.

3. The pulsed eddy current sensor probe of claim 2, wherein said connector is disposed on said sensor array board.

4. The pulsed eddy current sensor probe of claim 1, wherein said sensors form a linear array on said sensor array board.

5. The pulsed eddy current sensor probe of claim 4, further comprising a magnetic shielding disposed between said sensors and said drive coil.

6. The pulsed eddy current sensor probe of claim 1, wherein said sensors form a linear array on said sensor array board.

7. The pulsed eddy current sensor probe of claim 6, wherein said sensors comprise giant magnetoresistance (GMR) sensors.

8. The pulsed eddy current sensor probe of claim 7, wherein said drive coil extends around said linear array of GMR sensors and is operable to generate a magnetic flux that is oriented in a direction substantially along the axis of sensitivity of the GMR sensors.

9. The pulsed eddy current sensor probe of claim 8, further comprising a magnetic shielding disposed between said sensors and said drive coil.

10. The pulsed eddy current sensor probe of claim 1, wherein said sensor array board comprises a printed circuit board.

11. A pulsed eddy current sensor probe comprising:
a plurality of sensor array boards;
a plurality of sensors arranged in a linear array on each of said sensor array boards and operable to sense and generate output signals from the transient electromagnetic flux in a part being inspected, each of said sensors having a differential output comprising a positive and a negative output, wherein said sensors are positioned at an edge of each of said sensor array boards to form the respective linear arrays, wherein each of said sensors has an axis of sensitivity that is oriented substantially normal to said edge of the respective sensor array board;
a plurality of drive coils disposed adjacent to said sensors and operable to transmit transient electromagnetic flux into the part being inspected;
a plurality of first multiplexers; and
a plurality of second multiplexers, each of said first and second multiplexers being arranged on a respective one of said sensor array boards and operable to switch between said sensors on the respective sensor array board, wherein each of said first multiplexers is connected to the positive outputs of said sensors on the respective sensor array board,
wherein each of said second multiplexers is connected to the negative outputs of said sensors on the respective sensor array board, and
wherein said sensor array boards are arranged to form a two-dimensional sensor array.

12. The pulsed eddy current sensor probe of claim 11, wherein at least one drive coil is connected to a respective one of each of said sensor array boards.

13. The pulsed eddy current sensor probe of claim 11, further comprising a plurality of connectors, wherein at least one of said connectors is disposed on each of said sensor array boards, and wherein each of said connectors is operable to connect to said first and second multiplexers on the respective one of said sensor array boards.

14. The pulsed eddy current sensor probe of claim 11, wherein each of said drive coils extends around the respective linear array of sensors and is operable to generate a magnetic field that is oriented in a direction substantially along the axis of sensitivity of the sensors.

15. The pulsed eddy current sensor probe of claim 14, wherein said sensors comprise giant magnetoresistance (GMR) sensors.

16. The pulsed eddy current sensor probe of claim 14, further comprising a plurality of magnetic shieldings, each of said magnetic shieldings being disposed between said sensors and the respective one of said drive coils.

17. A pulsed eddy current sensor probe comprising:
a plurality of sensor array boards;
a plurality of sensors arranged in a linear array on each of said sensor array boards and operable to sense and generate output signals from the transient electromagnetic flux in a part being inspected, each of said sensors having a differential output comprising a positive and a negative output;
a plurality of drive coils disposed adjacent to said sensors and operable to transmit transient electromagnetic flux into the part being inspected;
a plurality of first muitiplexers; and
a plurality of second multiplexers, each of said first and second multiplexers being arranged on a respective one of said sensor array boards and operable to switch between said sensors on the respective sensor array board, wherein each of said first multiplexers is connected to the positive outputs of said sensors on the respective sensor array board, wherein each of said second multiplexers is connected to the negative outputs of said sensors on the respective sensor array board, a motherboard connected to each of said connectors, wherein said sensor array boards are arranged to form a two-dimensional sensor array.

18. The pulsed eddy current sensor probe of claim 17, further comprising a demultiplexer disposed on said motherboard, wherein at least one drive coil is connected to a respective one of each of said sensor array boards, and wherein said demultiplexer is operable to receive a plurality of control signals and a plurality of drive pulses and to selectively drive each of said drive coils in response to the control signals.

19. The pulsed eddy current sensor probe of claim 17, wherein at least one drive coil is connected to a respective one of each of said sensor array boards, said pulsed eddy current sensor probe further comprising an enabling circuit adapted to selectively enable a respective one of said sensor array boards via the respective one of said connectors for driving the respective one of said drive coils and for collecting a plurality of output signals using the sensors arranged in said linear array on the respective sensor array board.

20. The pulsed eddy current sensor probe of claim 19, wherein said enabling circuit comprises a demultiplexer disposed on said motherboard, wherein said demultiplexer is operable to receive a plurality of control signals and a plurality of drive pulses and to selectively drive each of said drive coils in response to the control signals via the respective connector.

21. The pulsed eddy current sensor probe of claim 20, wherein said enabling circuit further comprises a plurality of switches.

22. A method of inspecting a part comprising:

positioning a linear array of sensors adjacent to a surface of the part, wherein each of the sensors has an axis of sensitivity aligned substantially normal to the surface of the part;

generating a magnetic flux that is oriented in a direction substantially along the axis of sensitivity of the sensors to transmit transient electromagnetic flux into the part;

sensing the transient electromagnetic flux in the part being inspected;

generating a differential output signal using one of the sensors, wherein said generation of the magnetic field and said sensing and generating the differential output signal using one of the sensors are repeated for at least a subset of the sensors in the linear array to acquire a plurality of the differential output signals, each of the differential output signals comprising a positive and a negative output;

indexing and storing the differential output signals to indicate the respective sensors used to generate the differential output signals;

generating a calibration curve for each of the sensors;

calculating a plurality of informative parameter values for the differential output signals, each of the informative parameter values being associated with a respective one of the sensors; and comparing the informative parameter values with the respective calibration curves.

23. The inspection method of claim 22, wherein the linear array of sensors is disposed on a sensor array board, said inspection method further comprising performing on-board multiplexing to switch between the sensors.

24. A method of inspecting a part comprising:

positioning a two dimensional sensor array adjacent to a surface of the part, wherein the two dimensional sensor array comprises a plurality of linear arrays of sensors, wherein each of the linear arrays is disposed on a respective one of a plurality of sensor array boards, and wherein each of the sensors has an axis of sensitivity aligned substantially normal to the surface of the part;

generating a magnetic flux that is oriented in a direction substantially along the axis of sensitivity of the sensors to transmit transient electromagnetic flux into the part;

sensing the transient electromagnetic flux in the part being inspected and generating a differential output signal using one of the sensors, wherein said generation of the magnetic field and said sensing and generating the differential output signal using one of the sensors are repeated for at least a subset of the sensors in respective ones of at least a subset of the linear arrays to acquire a plurality of the differential output signals, each of the differential output signals comprising a positive and a negative output; and performing on-board multiplexing to switch between the sensors within a respective one of the linear arrays.

25. The inspection method of claim 24, further comprising indexing and storing the differential output signals to indicate the respective sensors used to generate the differential output signals.

26. The inspection method of claim 25, further comprising:

generating a calibration curve for each of the sensors;

calculating a plurality of informative parameter values for the differential output signals, each of the informative parameter values being associated with a respective one of the sensors in the two dimensional sensor array; and comparing the informative parameter values with the respective calibration curves.

27. The inspection method of claim 24, wherein a drive coil is disposed on each of the sensor array boards, the inspection method further comprising:

enabling a respective one of the sensor array boards;

selectively driving the drive coil on the respective sensor array board to generate the magnetic field for transmitting transient electromagnetic flux into the part; and collecting the differential output signals using the sensors in the linear array on the respective sensor array board, wherein the steps of enabling, selectively driving and collecting are repeated for each of the sensor array boards for collecting the differential output signals from the sensors within each of the linear arrays forming the two dimensional sensor array.

* * * * *